United States Patent [19]

Baumann et al.

[11] 3,931,271

[45] Jan. 6, 1976

[54] PROCESS FOR THE PRODUCTION OF SECONDARY ALCOHOL ETHER SULFATES

[75] Inventors: Horst Baumann, Leichlingen; Wilfried Umbach, Langenfeld; Werner Stein, Erkrath-Unterbach, all of Germany

[73] Assignee: Henkel & Cie G.m.b.H., Dusseldorf, Holthausen, Germany

[22] Filed: Feb. 24, 1971

[21] Appl. No.: 118,549

[30] Foreign Application Priority Data
Apr. 8, 1970 Germany............................ 2016656

[52] U.S. Cl................ 260/458; 252/551; 260/615 B
[51] Int. Cl.² ............... C07C 139/00; C07C 139/10; C07C 141/00
[58] Field of Search ..................................... 260/458

[56] References Cited
UNITED STATES PATENTS 2,174,761  10/1939  Schuette et al. ................... 260/458
3,413,331  11/1968  Beiser et al. ........................ 260/458
3,755,407  8/1973  Wilkes ................................ 260/458

FOREIGN PATENTS OR APPLICATIONS 748,570  5/1956  United Kingdom................. 260/458
797,119  6/1958  United Kingdom................. 260/458

*Primary Examiner*—Norman Morgenstern
*Attorney, Agent, or Firm*—Hammond & Littell

[57] ABSTRACT

A process for the production of secondary alcohol ether sulfates which consists essentially of reacting adducts of secondary alkanols having from 6 to 22 carbon atoms adducted with 1 to 10 mols of an alkylene oxide selected from the group consisting of ethylene oxide and propylene oxide, said adduct having at least 1 mol of oxypropylene per mol of alcohol, with at least a molecular equivalent of a sulfating agent stronger than concentrated sulfuric acid at temperatures of from 0°C to 50°C and recovering said secondary alcohol ether sulfate.

8 Claims, No Drawings though it is known on the introduction of propylene glycol ether groups by propoxylation, adducts with predominately secondary hydroxyl groups are formed. Therefore, the same difficulties in the further reaction of these adducts, especially in sulfation, would be expected as in the sulfation of secondary alcohols themselves. With this expectation, the sulfation of secondary alcohol propoxylates would appear to the expert as having little prospect of good yields.

PROCESS FOR THE PRODUCTION OF SECONDARY ALCOHOL ETHER SULFATES

THE PRIOR ART

At present secondary alcohols can be prepared from inexpensive raw materials, such as by oxidation of paraffins, substantially simpler than the preparation of primary alcohols. However, up to now the practical use of secondary alcohols is limited to non-ionic products prepared from them. Surface-active sulfates derived from secondary alcohols are used only in small amounts since the preparation of such raw materials for washing agents is very difficult, because of the instability of the secondary alkylsulfates. Primary alcohols, on the contrary, can be converted simply and with good yields into surface-active sulfates. In the sulfation of secondary alcohols, the conversion rates are low. In order to obtain somewhat usable products, expensive procedures have to be introduced, such as working with solvents and adduct formers, the use of special sulfating agents, such as, for example, amidosulfonic acid, etc., as well as the addition of ethylene oxide adducts of primary alcohols. On the other hand, there is the possibility that by reaction of secondary alcohols with ethylene oxide, adducts with primary hydroxyl groups can be prepared, the sulfation products of which could be expected to have greater stability.

It is, however, very difficult to prepare ethoxylates of secondary alcohols with a high conversion rate and small amounts of by-products. A higher conversion rate of the secondary alcohols with ethylene oxide can only be attained by relatively cumbersome procedures, such as, for example, a two-step ethoxylation in which in the first step an acidic catalyst is used and, after distilling off the unreacted secondary alcohol, in the second step an alkaline catalyst is utilized. However, the ethoxylated secondary alcohols obtained by this expensive procedure are also unsatisfactorily sulfated and can only be sulfated by the application of special procedures. This is difficult to explain since by the ethoxylation of secondary alcohols, adducts with primary hydroxyl groups were formed.

OBJECTS OF THE INVENTION

An object of the present invention is the development of a simple process for the production of secondary alcohol ether sulfates utilizing conventional strong sulfating agents to give products with a high degree of sulfation.

Another object of the invention is the development of a process for the production of secondary alcohol ether sulfates which consists essentially of reacting adducts of secondary alkanols having from 6 to 22 carbon atoms adducted with 1 to 10 mols of an alkylene oxide selected from the group consisting of ethylene oxide and propylene oxide, said adduct having at least 1 mol of oxypropylene per mol of alcohol, with at least a molecular equivalent of a sulfating agent stronger than concentrated sulfuric acid at temperatures of from 0°C to 50°C and recovering said secondary alcohol ether sulfate.

These and other objects of the invention will become more apparent as the description thereof proceeds.

DESCRIPTION OF THE INVENTION

It has now been surprisingly found that alkylene oxide adducts of secondary alcohols which contain at least one propylene glycol ether group can be sulfated simply with a high conversion rate. This result was the more unexpected since, as is known, on the introduction of propylene glycol ether groups by propoxylation, adducts with predominately secondary hydroxyl groups are formed. Therefore, the same difficulties in the further reaction of these adducts, especially in sulfation, would be expected as in the sulfation of secondary alcohols themselves. With this expectation, the sulfation of secondary alcohol propoxylates would appear to the expert as having little prospect of good yields.

The invention relates, therefore, to a process for the preparation of surface-active ether and polyether sulfates which is characterized in that adducts of secondary alkanols having 6 to 22 carbon atoms adducted with 1 to 10 mols of alkylene oxide, possessing in the average at least 1 mol of propylene oxide per mol of alcohol, are reacted in a known manner at temperatures between 0°C and 50°C, particularly from 10°C and 30°C, with strong sulfating agents in at least stoichiometric amounts.

As starting materials those adducts may be used that were obtained (1) by ethoxylation of secondary alcohols in the first step and subsequent propoxylation of the reaction mixtures, or (2) by reaction of secondary alcohols with ethylene oxide/propylene oxide mixtures, or (3) by the ethoxylation of reaction mixtures of secondary alcohols with propylene oxide, or (4) by pure propoxylation of secondary alcohols. The preferred starting materials are the adducts of propylene oxide to secondary alcohols or secondary alkanol propoxylates having 6 to 22 carbon atoms in the alkanol and 1 to 10 oxypropylene units.

The mixed alkoxylates to be used contain preferably 1 to 4, particularly 2 to 3, oxyethylene groups. Of particular advantage among the pure propylene oxide adducts are those substance mixtures which were obtained by reaction of 1.5 to 5 mols of propylene oxide with 1 mol of secondary alcohol.

The starting materials can be obtained by conventional alkoxylation methods. The alkoxylation can be carried out both anionically, in the presence of alkaline alkoxylation catalysts, such as alkali metal hydroxides or alkali metal alcoholates, particularly sodium, potassium and lithium lower alkanolates, and cationically in the presence of acidic catalysts, such as $BF_3$, or in the presence of the tertiary oxonium salts described as alkoxylation catalysts in Belgian Pat. No. 715,048.

If mixed adducts are used which have been obtained by propoxylation of ethylene oxide adducts of secondary alcohols as starting materials, such mixed adducts are preferred in which the alkoxylation in the first step was carried out by a cationic catalyst and in the second step with an anionic catalyst.

Among the mixed adducts which are obtained by simultaneous addition of ethylene oxide and propylene oxide, or by propoxylation in the first step and ethoxylation in the second step, as well as in the pure propoxylation products, these are preferably prepared by reaction with an anionic catalyst.

The secondary alcohols utilized to prepare the alkoxylation mixtures can be either compounds of uniform chain length or mixtures of homologs. Of particular economic advantage are those alcohol mixtures which have been obtained by the oxidation of paraffins in the presence of boron compounds, such as, for example, boric acid, boron trioxide, borates, boric acid esters, as well as other known reagents for the formation of secondary alcohols, such as arsenic acid, arsenic acid esters, arsenic trioxide, and others.

The alkoxylation mixtures utilizable for the subsequent sulfation can be used as crude products, that is, without intervening purification or processing operations. This is of essential importance for the technical execution of the process. These crude alkoxylation mixtures contain, therefore, in addition to the desired alkylene oxide adducts of secondary alcohols, as secondary constituents, the corresponding alkylene and/or polyalkylene glycols as well as, possibly, non-reacted secondary alcohol. The sulfation of the alkoxylate mixture is preferably carried out in the temperature range of from 10°C to 30°C.

By "strong sulfating agents" are meant those which are stronger than concentrated sulfuric acid, for example, $SO_3$ or $SO_3$/air mixtures, oleum, chlorosulfonic acid, and the like. The addition of adduct formers for the sulfating agent or the presence of solvents are not required in the process. The preferred sulfating agent is chlorosulfonic acid. The mol ratio between the alkoxylate and the sulfating agent is advantageously chosen in the range of from 1:1.0 to 1:1.2, particularly in the range of from 1:1.02 to 1:1.1.

The sulfation reaction can be carried out continuously or discontinuously. The reaction times lie between fractions of seconds to about 20 minutes, depending upon the sulfating agent and/or sulfating apparatus used. Particularly short reaction times are attained if the reaction is carried out with very strong sulfating agents, such as $SO_3$/air mixtures, in modern short-time sulfation reactors which operate by the splitring or falling film principle.

The products of the process have a substantially higher degree of sulfation than the products obtained by the sulfation of technical ethylene oxide adducts of secondary alcohols. They have, without further processing, very good surface-active properties and are superior, particularly in regard to their wetting action, to the known commercial sulfated adducts of ethylene oxide to primary alcohols.

The advantages attainable with the invention consist primarily in that as a raw material source for surface-active, water-soluble sulfates, secondary alcohols have been made available. Particularly those secondary alcohols which are easily obtainable by paraffin oxidation in the presence of the above-named oxidation catalysts to produce secondary alcohols with statistically distributed hydroxyl groups. These alcohols are converted by alkoxylation to the substances suitable for sulfation. Thus, these petrochemical raw materials can form the basis for the desired surface-active substances. Anionic active derivatives of secondary alcohols were up to now technically not producible by a simple way although secondary alcohols have been produced for some time on a large scale. The use of secondary alcohols was, therefore, until now limited to the production of non-ionic substances.

A further advantage of the process according to the invention can be seen in that the necessary alkoxylation may be carried out without a large expense in regard to catalysts and/or equipment.

The following examples are illustrative of the invention without being deemed limitative in any respect.

EXAMPLES

The results of the sulfation of propoxylated and ethoxylated-propoxylated adducts of secondary alcohols are summarized in the following Table I. The starting alkoxylated secondary alcohol mixtures are prepared in a known manner by the reaction of 2 to 6 mols of alkylene oxides with, each time, 1 mol of a secondary $C_{14}$-$C_{15}$ alcohol (composition less than $C_{14}$, 1.8%; $C_{14}$, 74.1%; $C_{15}$, 24.1%; OH-number 250, average molecular weight = 218), obtained by the oxidation of paraffin in the presence of boric acid, in the presence of each time of 0.2% by weight (in reference to the alcohol used) of the named catalysts at a reaction temperature for the alkaline catalysts of 140°C and for the other catalysts of 5°C to 50°C. The ethoxylated-propoxylated adducts were obtained either by a two-stage addition of the different alkylene oxides or by reaction with ethylene oxide-propylene oxide mixtures.

The crude alkoxylation products obtained were charged in amounts of 1.5 mols each time into a 3-neck 1.5 liter flask, provided with a stirrer, a gas-inlet tube reaching to the flask bottom, a dropping funnel, and a thermometer. 1.5 to 1.65 mols of chlorosulfonic acid were added under strong agitation, at temperatures between 10°C and 30°C, over a period of about 10 minutes, while simultaneously passing through a slight nitrogen stream for the removal of the evolving hydrogen chloride. After the addition of the chlorosulfonic acid was completed, the agitation was continued for another 5 minutes with nitrogen passing through. Subsequently, the liquid reaction mixture was added to an aqueous sodium hydroxide solution in excess for neutralization. The degree of sulfation was determined in an aliquot part of the mixture by extraction of an aqueous alcoholic solution of the mixture five times with petroleum ether. The sulfated products obtained were, in the form of 30% aqueous preparations, viscous, clear pastes.

TABLE I

| Example No. | Alkylene Oxide | Adducted Amount of alkylene Oxide | Alkoxylation Catalyst | Degree of Sulfation |
|---|---|---|---|---|
| 1 | Propylene Oxide | 2.0 | Sodium methoxide | 88.5 % |
| 2 | " | 3.0 | " | 91.5 % |
| 3 | " | 4.0 | " | 93.0 % |
| 4 | " | 5.0 | " | 93.7 % |
| 5 | " | 2.0 | Boron trifluoride | 90.5 % |
| 6 | " | 3.0 | " | 91.4 % |
| 7 | " | 4.0 | " | 92.4 % |
| 8 | " | 5.0 | " | 93.3 % |
| 9 | 1) Propylene Oxide | 3.0 | Sodium methoxide | 93.2 % |
|   | 2) Ethylene Oxide | 1.0 | " | |
| 10 | 1) Propylene Oxide | 4.0 | Sodium methoxide | 94.7 % |
|   | 2) Ethylene Oxide | 2.0 | " | |

TABLE I-continued

| Example No. | Alkylene Oxide | | Adducted Amount of alkylene Oxide | Alkoxylation Catalyst | Degree of Sulfation |
|---|---|---|---|---|---|
| 11 | | 1) Propylene Oxide | 3.0 | Boron trifluoride | 90.9 % |
| | | 2) Ethylene Oxide | 1.0 | Sodium methoxide | |
| 12 | | 1) Propylene Oxide | 4.0 | Boron trifluoride | 93.3 % |
| | | 2) Ethylene Oxide | 2.0 | Sodium methoxide | |
| 13 | | 1) Propylene Oxide | 4.0 | Triethyloxoniumfluoroborate | 92.8 % |
| | | 2) Ethylene Oxide | 2.0 | Sodium methoxide | |
| 14 | | 1) Ethylene Oxide | 1.0 | Sodium methoxide | 92.9 % |
| | | 2) Propylene Oxide | 3.0 | '' | |
| 15 | | 1) Ethylene Oxide | 2.0 | Sodium methoxide | 94.5 % |
| | | 2) Propylene Oxide | 4.0 | '' | |
| 16 | | 1) Ethylene Oxide | 1.0 | Boron trifluoride | 91.9 % |
| | | 2) Propylene Oxide | 3.0 | Sodium methoxide | |
| 17 | | 1) Ethylene Oxide | 2.0 | Boron trifluoride | 92.8 % |
| | | 2) Propylene Oxide | 4.0 | Sodium methoxide | |
| 18 | | 1) Ethylene Oxide | 2.0 | Triethyloxoniumfluoroborate | 93.2 % |
| | | 2) Propylene Oxide | 4.0 | Sodium methoxide | |
| 19 | | 1) Ethylene Oxide | 3.0 | Boron trifluoride | 92.0 % |
| | | 2) Propylene Oxide | 3.0 | Sodium methoxide | |
| 20 | mixt. | Ethylene Oxide | 1.0 | Boron trifluoride | 91.2 % |
| | | Propylene Oxide | 3.0 | | |
| 21 | mixt. | Ethylene Oxide | 1.0 | Triethyloxoniumfluoroborate | 92.0 % |
| | | Propylene Oxide | 3.0 | | |
| 22 | mixt. | Ethylene Oxide | 2.0 | Boron trifluoride | 90.5 % |
| | | Propylene Oxide | 4.0 | | |
| 23 | mixt. | Ethylene Oxide | 3.0 | Sodium methoxide | 93.6 % |
| | | Propylene Oxide | 3.0 | | |
| 24 | mixt. | Ethylene Oxide | 2.0 | Sodium methoxide | 95.3 % |
| | | Propylene Oxide | 4.0 | | |
| 25 | mixt. | Ethylene Oxide | 2.0 | Sodium methoxide | 94.2 % |
| | | Propylene Oxide | 2.0 | | |
| 26 | mixt. | Ethylene Oxide | 3.0 | Sodium methoxide | 93.9 % |
| | | Propylene Oxide | 1.0 | | |
| 27 | mixt. | Ethylene Oxide | 4.0 | Sodium methoxide | 96.0 % |
| | | Propylene Oxide | 2.0 | | |

COMPARATIVE TESTS

For comparison the following named addition products of ethylene oxide to the above-named secondary alcohol $C_{14}$-$C_{15}$ alcohol were sulfated in the same way.

TABLE II

| Comparative Example No. | Adducted Amount of Ethylene Oxide | Ethoxylation Catalyst | Degree of Sulfation |
| --- | --- | --- | --- |
| A | 2.0 | Sodium methoxide | 68.8 % |
| B | 2.1 | Boron trifluoride | 81.7 % |
| C | 3.0 | Triethyl oxonium fluoroborate | 85.4 % |

EXAMPLE 9

Tests were carried out with the products according to Examples 1, 2, 5, 6 and 7 for the determination of the textile wetting time.

The following test method was utilized. Disks of test fabric of 35 mm diameter were introduced with the aid of a plunger into solution always containing 1 gm of the test substance. The time when the fabric was completely wetted, that is, when it detached itself from the plunger and sank was measured. As test fabric a duck cloth of unbleached cotton was used. For the preparation of the solutions distilled water was used. For comparison analogous tests were carried out with solutions of a sulfated adduct of 2 mols ethylene oxide to 1 mol of a primary $C_{12}$-$C_{14}$ alcohol which is commercially available under the name "Texapon N 25". The results are summarized in the following Table III.

TABLE III

| Sulfonate according to Example No. | Wetting Time seconds |
| --- | --- |
| 1 | 31 |
| 2 | 32 |
| 5 | 23 |
| 6 | 27 |
| 7 | 33 |
| Texapon N 25 | 40 |

The superiority of the products according to the invention can be seen from the shorter wetting time compared to Texapon N 25.

The preceding specific embodiments are illustrative of the practice of the invention. It is to be understood, however, that other expedients known to those skilled in the art may be employed without departing from the spirit of the invention or the scope of the appended claims.

We claim:

1. A process for the production of secondary alcohol ether sulfates which consists essentially of reacting crude adducts of secondary alkanols having from 6 to 22 carbon atoms adducted with 1 to 10 mols of an alkylene oxide selected from the group consisting of ethylene oxide and propylene oxide, said crude adduct having at least 1 mol of oxypropylene per mol of alcohol and being obtained from the oxyalkylation reaction without intervening purification, with from 1.0 to 1.2 mols per mol of said crude adduct, of a sulfating agent stronger than concentrated sulfuric acid selected from the group consisting of sulfur trioxide, sulfur trioxide/air mixtures, oleum and chlorosulfonic acid, at temperatures of from 10°C to 30°C, and recovering said secondary alcohol ether sulfate having a high degree of sulfation.

2. The process of claim 1 wherein said crude adduct of said secondary alkanol is a propylene oxide adduct containing from 1.5 to 5 mols of propylene oxide per mol of secondary alkanol.

3. The process of claim 1 wherein said secondary alkanol was prepared by the oxidation of a paraffin.

4. The process of claim 1 wherein said sulfating agent stronger than concentrated sulfuric acid is chlorosulfonic acid.

5. The process of claim 1 wherein said sulfating agent stronger than sulfuric acid is utilized in an amount of from 1.02 to 1.1 mols per mol of said crude adduct of said secondary alkanol.

6. The process of claim 1 wherein said crude adduct of said secondary alkanol is first adducted with propylene oxide and then with from 1 to 4 mols of ethylene oxide.

7. The process of claim 1 wherein said crude adduct of said secondary alkanol is first adducted with from 1 to 4 mols of ethylene oxide and then with said propylene oxide.

8. The process of claim 1 wherein said crude adduct of said secondary alkanol is adducted with a mixture of from 1 to 4 mols of ethylene oxide and said propylene oxide.

* * * * *